(12) United States Patent
Nakajima et al.

(10) Patent No.: US 11,735,334 B2
(45) Date of Patent: Aug. 22, 2023

(54) STRETCHABLE WIRE TAPE FOR TEXTILE, WEARABLE DEVICE, AND METHOD FOR PRODUCING TEXTILE HAVING WIRES

(71) Applicant: XENOMA INC., Tokyo (JP)

(72) Inventors: Masao Nakajima, Tokyo (JP); Naomi Ohto, Tokyo (JP)

(73) Assignee: XENOMA INC., Tokyo (JP)

(*) Notice: Subject to any disclaimer, the term of this patent is extended or adjusted under 35 U.S.C. 154(b) by 906 days.

(21) Appl. No.: 16/627,623

(22) PCT Filed: Dec. 27, 2017

(86) PCT No.: PCT/JP2017/046940
§ 371 (c)(1),
(2) Date: Dec. 30, 2019

(87) PCT Pub. No.: WO2019/130477
PCT Pub. Date: Jul. 4, 2019

(65) Prior Publication Data
US 2020/0157713 A1 May 21, 2020

(51) Int. Cl.
*H01B 7/00* (2006.01)
*H01B 7/08* (2006.01)
(Continued)

(52) U.S. Cl.
CPC ............. *H01B 7/0838* (2013.01); *H01B 7/06* (2013.01); *H01B 13/008* (2013.01);
(Continued)

(58) Field of Classification Search
CPC ...... H01B 7/0838; H01B 7/06; H01B 13/008; H05K 1/0283; D10B 2401/16; D10B 2403/0311
See application file for complete search history.

(56) References Cited

U.S. PATENT DOCUMENTS

2011/0088925 A1* 4/2011 Tatsumi ................ H01B 7/06
174/69
2017/0053894 A1 2/2017 Park et al.
(Continued)

FOREIGN PATENT DOCUMENTS

JP          5808919 B      11/2015
JP          5993493 B       9/2016
(Continued)

OTHER PUBLICATIONS

WO 2016133065 A1 English Translation (Year: 2016).*
(Continued)

*Primary Examiner* — Pete T Lee
(74) *Attorney, Agent, or Firm* — Crowell & Moring LLP

(57) ABSTRACT

Provided are a stretchable wire tape for a textile that can maintain high levels in all of stretchability, electrical conductivity, durability, an insulating property, and design and can also have a reduced production cost, wearable devices, and a method for producing textiles having wires. The stretchable wire tape for the textile includes a stretchable electrically conductive wire, and stretchable insulating films each including a first face and a second face opposite to the first face, the stretchable insulating films being bonded to opposite sides of the stretchable electrically conductive wire on their first faces. Since the stretchable insulating films are bonded to the opposite sides of the stretchable electrically conductive wire via bonding layers, durability and an insulating property can be secured while stretchability and electrical conductivity of the electrically conductive wire can be maintained, and design can also be improved.

8 Claims, 6 Drawing Sheets

(51) Int. Cl.
  *H01B 7/06* (2006.01)
  *H01B 13/008* (2006.01)
  *H05K 1/02* (2006.01)
(52) U.S. Cl.
  CPC ....... *H05K 1/0283* (2013.01); *D10B 2401/16* (2013.01); *D10B 2403/0311* (2013.01)

(56) References Cited

U.S. PATENT DOCUMENTS

| | | |
|---|---|---|
| 2018/0033520 A1 | 2/2018 | Yoshida et al. |
| 2018/0073172 A1 | 3/2018 | Kurahashi et al. |
| 2019/0053372 A1 | 2/2019 | Kwon |
| 2019/0075652 A1* | 3/2019 | Nakajima ............ A61B 5/0205 |

FOREIGN PATENT DOCUMENTS

| | | | |
|---|---|---|---|
| JP | 2017-144239 A | 8/2017 | |
| WO | WO 2009/157070 A1 | 12/2009 | |
| WO | WO 2016/133065 A1 | 8/2016 | |
| WO | WO-2016133065 A1 * | 8/2016 | ............. H01B 13/00 |

OTHER PUBLICATIONS

Extended European Search Report for Europe Application No. 17936255.3, dated Sep. 21, 2020, 8 pages.
Office Action in Japan Application 2021-041371 dated Jan. 4, 2022 3 pages.

* cited by examiner

STRETCHABLE WIRE TAPE FOR TEXTILE, WEARABLE DEVICE, AND METHOD FOR PRODUCING TEXTILE HAVING WIRES

This application is a 371 application of PCT/JP2017/046940 having an international filing date of Dec. 27, 2017, the entire content of which is incorporated herein by reference.

TECHNICAL FIELD

The present invention relates to stretchable wire tapes for textiles, wearable devices, and a method for producing textiles having wires.

BACKGROUND ART

In recent years, research and development of a garment-shaped wearable device including stretchable wires and sensors have been advanced. For example, such garment-shaped wearable device is obtained by forming stretchable wires on a material of a garment and connecting them to sensors, bioelectrodes, actuators, and controllers so that information such as motions of the wearer, and biological information such as pulses of the wearer, can be obtained, or feedback can be provided to the wearer through vibration, for example.

As a method for forming such stretchable wires on a material of a garment, there have been proposed a method of directly sewing a stretchable wire material into a material of a garment (see Patent Literature 1) and a method of interweaving electrically conductive wires into a material of a garment using a structure that can impart stretchability to the wires (see Patent Literature 2). Stretchable wires are required to have properties, such as stretchability and electrical conductivity as well as durability against repeated stretch, an insulating property for preventing short between the wires due to sweat, and compatibility with restrictions on the design of the wires, with a good balance, and are also requited to be produced easily and at low cost.

The method proposed in Patent Literature 1 is a method of providing an insulating property to a stretchable wire using a covering, but the diameter of the stretchable wire is increased and the productivity is low and the design of the garment is restricted, since the stretchable wire is directly sewn into a garment. Further, it is concerned that the wire may get caught on the wearer while the wearer is putting on the garment and thus may break. Meanwhile, the method proposed in Patent Literature 2 has a problem in stretchability because when wires are buried in stretchable resin via an adhesive, for example, to secure an insulating property, the adhesive will soak through knitted stitches, which in turn may disturb structural deformation of the wires. Further, since the adhesive becomes a point of stress concentration, the wires would likely break easily, which also poses a problem in durability.

CITATION LIST

Patent Literature

Patent Literature 1: JP 5808919 B
Patent Literature 2: JP 5993493 B

SUMMARY OF INVENTION

Technical Problem

In view of the foregoing problems, an object of the present invention is to provide stretchable wire tapes for textiles that can maintain high levels in all of stretchability, electrical conductivity, durability, an insulating property, and design and can also have a reduced production cost, wearable devices, and a method for producing textiles having wires.

Solution to Problem

In view of the foregoing, a stretchable wire tape for a textile according to an embodiment of the present invention includes a stretchable electrically conductive wire, and stretchable insulating films each having a first face and a second face opposite to the first face, the stretchable insulating films being bonded to opposite faces of the stretchable electrically conductive wire on their first faces via bonding layers.

According to the present invention, since the stretchable insulating films are bonded to the opposite faces of the stretchable electrically conductive wire via bonding layers, the durability and insulating property of the stretchable electrically conductive wire can be secured. In addition, since the wire tape can be sequentially arranged on a wearable device in accordance with a desired wire layout, the design flexibility of the wire is high and the production cost can be reduced without wasting materials.

The stretchable wire tape for the textile preferably further includes a hot-melt bonding layer formed on the second face of each stretchable insulating film. According to such a configuration, the stretchable wire tape for the textile can be bonded to the substrate through pressure bonding with heat applied thereto.

The stretchable electrically conductive wire in the stretchable wire tape for the textile includes a stretchable core and at least one electrically conductive wire wound around the stretchable core. According to such a configuration of the stretchable electrically conductive wire, both high stretchability and high electrical conductivity can be achieved.

In addition, in the stretchable wire tape for the textile according to the present invention, a plurality of stretchable electrically conductive wires arranged in parallel can be arranged approximately in parallel without being in contact with each other. Further, the stretchable wire tape for the textile may include a stretchable non-electrically conductive wire(s) arranged between the plurality of stretchable electrically conductive wires, and the stretchable electrically conductive wires and the stretchable non-electrically conductive wire(s) may be alternately arranged. According to such a configuration, a plurality of stretchable electrically conductive wires can be arranged with an insulating property maintained within a single stretchable wire tape for a textile. It should be noted that the stretchable non-electrically conductive wire preferably includes a stretchable insulating core and a non-electrically conductive wire wound around the core. In addition, the stretchable electrically conductive wires are preferably arranged at a pitch of approximately 1.27 mm or a pitch of approximately 2.54 mm. Herein, the "pitch of approximately 1.27 mm" means a pitch that allows an electronic circuit, which includes a plurality of electrode pads arranged at intervals of 1.27 mm, to be connected without connection failures or short, and means a predetermined width, and so is "approximately 2.54 mm."

In addition, a wearable device according to the present invention includes a stretchable electrically conductive wire tape bonded to a fabric, and a plurality of sensors connected to the stretchable electrically conductive wire tape. The stretchable wire tape includes a stretchable electrically conductive wire, and stretchable insulating films each including a first face and a second face opposite to the first face, the stretchable insulating films being bonded to opposite faces of the stretchable electrically conductive wire on their first faces via bonding layers.

A method for producing a textile having wires according to the present invention includes bonding a stretchable wire tape to a fabric by melting a hot-melt bonding layer, the stretchable wire tape including a stretchable electrically conductive wire and stretchable insulating films, the stretchable insulating films each including a first face and a second face opposite to the first face and being bonded to opposite faces of the stretchable electrically conductive wire on their first faces via bonding layers.

Advantageous Effects of Invention

The present invention with the aforementioned configuration provides a stretchable wire tape for a textile that can maintain high levels in all of stretchability, electrical conductivity, durability, an insulating property, and design and can also have a reduced production cost, wearable devices, and a method for producing textiles having wires.

DESCRIPTION OF EMBODIMENTS

Figure 1:
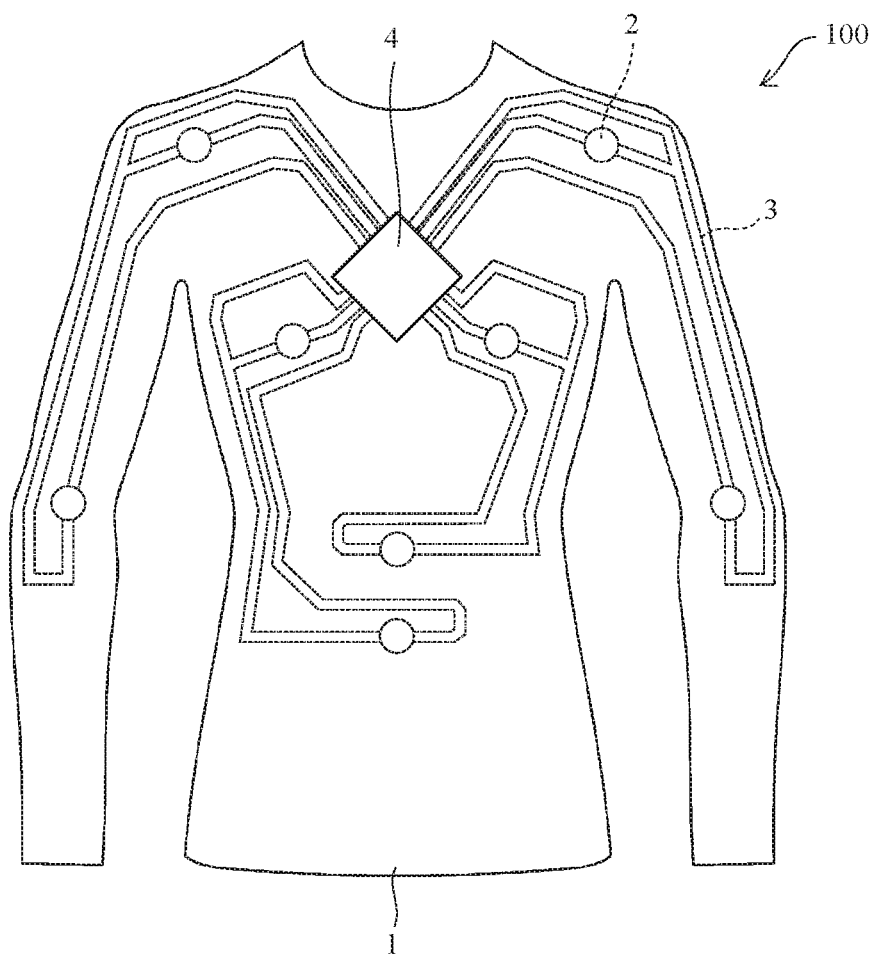
FIG. 1 is a schematic plan view of the configuration of a wearable device 100 according to the first embodiment.

Hereinafter, the present embodiment will be described with reference to the accompanying drawings. In the drawings, elements with the same functions may be denoted by the same reference numerals. Although the drawings illustrate embodiments and implementations according to the principle of the present disclosure, they are intended to be used for understanding of the present disclosure, and should never be used to narrowly construe the present disclosure. The description of this specification contains merely typical examples, and should never limit the scope of the claims or examples of the application of the present disclosure in any sense.

The present embodiment will be described in sufficient detail below for those skilled in the art to implement the present disclosure, but other implementations and embodiments are also possible, and changes to the configuration or structure as well as replacement of various elements is possible within the spirit and scope of the technical idea of the present disclosure. Therefore, the present disclosure should not be construed by being limited to the following descriptions.

First Embodiment

First, a stretchable wire tape for a textile, a wearable device, and a method for producing a textile having wires according to the first embodiment of the present invention will be described in detail with reference to FIG. 1 and the like.

FIG. 1 is a schematic plan view of the configuration of a wearable device 100 according to the first embodiment of the present invention. The wearable device 100 includes a substrate 1 with wire tapes 3 formed on its surface, a plurality of sensors 2 provided on the substrate 1, and a controller 4 that controls the plurality of sensors 2. The wires 3 electrically couple the sensors 2 and the controller 4. The upper and lower faces of the sensors 2 are covered with protective layers (not illustrated). The present embodiment will describe a case where the substrate 1 is a fabric for forming a garment, for example. The substrate 1 may also be a rubber sheet, for example, other than the fabric. It should be noted that the number of the controllers 4 need not be one, and more than one controller 4 may be provided on the single wearable device 100.

"Fabrics" as referred to in this specification mean wearable garments, for example. Specifically, fabrics refer to garments to be put on the upper body (e.g., garments with long sleeves, with three-quarter sleeves, with short sleeves, or without sleeves, or tank tops), garments to be put on the lower body (e.g., pants or skirts with heel length, ankle length, shin length, or knee length), one-piece garments (e.g., dresses or leotards), and accessories to be put on a part of the body (arm bands, wrist bands, knee bands, caps, or hats).

Such garments can be formed from various materials used for ordinary garments. For example, natural fibers, such as cotton, hemp, wool; chemical fibers, such as polyester, nylon, or acrylic; or mixed fibers of such materials can be used. It should be noted that the substrate 1 forming a garment is preferably in as close contact as possible with the wearer so that motions and biological information of the wearer can be detected with high sensitivity, for example. Therefore, the substrate 1 is preferably made of, though not limited thereto, a highly stretchable material obtained by mixing a base material, such as cotton or polyester fibers, with elastic fibers, such as polyurethane. In such a case, the mixing rate is preferably 1 to 50%, or more preferably, 3 to 30%.

The plurality of sensors 2 are disposed on the substrate 1. The sensors 2 are disposed on the substrate 1 at positions corresponding to the shoulders, elbows, back, or abdomen, for example, to detect motions of the wearer. The number and positions of the sensors 2 are appropriately selected in accordance with the intended use of the wearable device 100. In addition to the sensors 2, actuators may also be disposed on the substrate 1, though not illustrated. Further, bioelectrodes may also be disposed in addition to the sensors 2.

For each sensor 2, a temperature sensor, a strain sensor, a pressure sensor, a voice sensor, a photodiode, a piezoelectric element, or an inertial sensor can be used, for example. For each actuator, a vibration motor or a speaker can be used, for example. In addition, different sensors 2 or actuators may be used at different locations. Herein, examples of the inertial sensor include a 3-axis acceleration sensor that detects acceleration, a 3-axis gyroscope sensor that detects rotating speed, and a 3-axis terrestrial magnetism sensor that detects terrestrial magnetism to detect the absolute direction. Therefore, it can detect rotating motions or motions in the horizontal and vertical directions of the wearer. Such sensors may also be combined.

For each sensor 2, an analog sensor that can easily perform measurement can be used. The sensor 2 is not particularly limited as long as the amount of current flowing through the sensor 2, voltage applied to the sensor 2, the resistance of the sensor 2, and/or the capacitance of the sensor 2, for example, will change in response to changes in the physical quantity. Ideally, a variable-resistance sensor whose resistance and voltage applied across the sensor will change in response to changes in the physical quantity is used for the sensor 2 from the perspectives of simplicity of the circuit, for example. As the physical quantity, at least one of sound, light, temperature, pressure, or strain can be favorably used. In such a case, the resistance value of the sensor 2 is preferably 50 times or more that of the wire tape 3.

As an example of the analog sensor, a sensor that uses ink is preferably used. A sensor that uses ink is a sensor produced with ink that has been obtained by mixing electrically conducive particles in an elastomer solution or a dispersed material, for example. Printing such ink and drying it can obtain a sensor in which the electrically conducive particles are randomly dispersed in the elastomer film. Resistance across such a sensor will change as the distances between the electrically conductive particles change in response to tension applied, compression, or thermal expansion or shrinkage due to a temperature change. A sensor that uses ink is very thin and has high trackability with respect to a target to be measured. Therefore, accurate and stable measurement is possible.

The plurality of sensors 2 are connected by the wire tapes 3. The configuration of each wire tape 3 will be described later, but each wire tape 3 has a shape in which a stretchable electrically conductive wire is sandwiched between two insulating stretchable films via bonding layers.

The wire tapes 3 connected to the sensors 2 are connected to the controller 4. The controller 4 includes, as described below, connector portions connected to the wire tapes 3, and a circuit board having various circuits mounted thereon. With the functions of such circuits, the controller 4 gathers information detected by the sensors 2, and sends the information to the outside or records it on a recording medium. It should be noted that the number and arrangement of the sensors 2 and the controllers 4 illustrated in FIG. 1 are only exemplary, and are not limited thereto.

Figure 2:
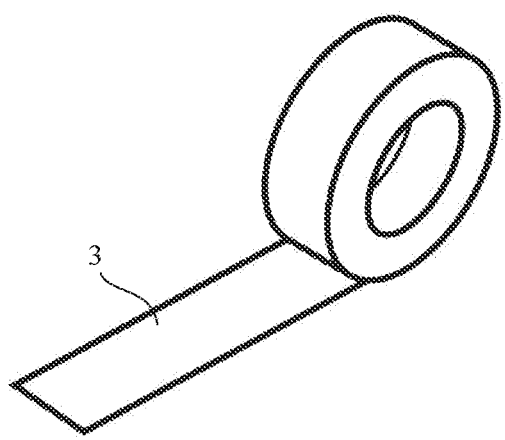
FIG. 2 is a perspective view illustrating the configuration of a wire tape 3 of the first embodiment.

Next, the configuration of each wire tape 3 of the first embodiment will be described with reference to FIGS. 2 and 3. The wire tape 3 is stored around a core (not illustrated) in a wound form or a spiral form as illustrated in FIG. 2 before it is bonded to the wearable device 100. When the wire tape 3 is bonded to the substrate 1, the wire tape 3 is reeled out from the core, and heat is applied to the substrate 1 using a heat welder that forms a feed mechanism together with a thermal head as described below so that a hot-melt bonding layer is melted by the heat and the wire tape 3 is bonded to the substrate 1. The length in the longitudinal direction of the rolled wire tape 3 may be set to greater than or equal to several ten cm, while the length in the shorter-side direction thereof may be set to a length is long enough to cover a stretchable wire 11 in the shorter-side direction. For example, the length in the shorter-side direction of the wire tape 3 can be set to about 5 to 20 mm.

Figure 3:
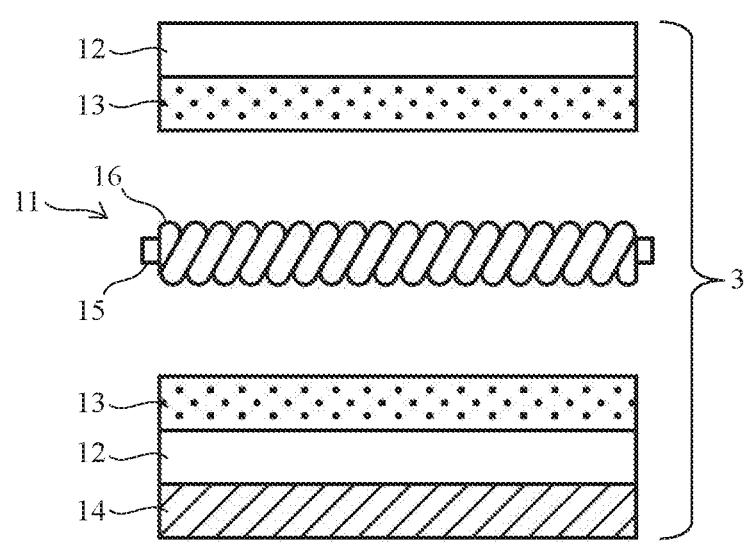
FIG. 3 is a schematic view illustrating the configuration of the wire tape 3 of the first embodiment.

FIG. 3 is a cross-sectional view illustrating the cross-sectional structure of the wire tape 3. The wire tape 3 includes a stretchable wire 11, stretchable insulating films 12, bonding layers 13, and a hot-melt bonding layer 14.

The stretchable wire 11 is a wire with predetermined stretchability and predetermined electrical conductivity. The stretchable wire 11 is connected to the aforementioned sensors 2 and the controller 4. Although FIG. 3 illustrates an example in which a single wire tape 3 includes only a single stretchable wire 11 arranged therein, it may also have two or more stretchable wires 11 arranged therein.

The stretchable insulating films 12 are bonded to the stretchable wire 11 via the respective bonding layers 13 while covering the opposite sides of the stretchable wire 11. By sandwiching the stretchable wire 11 together with the bonding layers 13, the stretchable insulating films 12 serve to prevent short between the stretchable wire 11 and the outside and prevent corrosion and damage to the stretchable wire 11. Therefore, the covering width is preferably in the range of 0.1 to 100 mm, or more preferably in the range of 0.5 to 5 mm from the outer periphery of the wire tape 3. If the covering width is too large, unnecessary portions will increase, which in turn can disturb air permeability of the wearable device. In contrast, if the covering width is too small, the possibility that the stretchable wire 11 may be partially exposed to the outside will increase, thus increasing the possibility of short.

The stretchability of each stretchable insulating film 12 is such that the amount of change in the shape of the stretchable insulating film 12 from the initial shape is preferably greater than or equal to 30%, more preferably, greater than or equal to 50%, and particularly preferably, greater than or equal to 100%. The thickness of each stretchable insulating film 12 is preferably 5 to 300 μm, or more preferably, 10 to 100 μm. The thickness in such a range can maintain high stretchability and strength. Examples of the materials of the stretchable insulating films 12 include a film and a sheet made of natural rubber or synthetic rubber. Among them, polyurethane rubber is preferable from the perspectives of stretchability, durability, heat resistance, and cost. The bonding layer 13 is preferably a stretchable rubber-based adhesive. This can improve the stretchability of the wire tape. In addition, a thermoplastic adhesive can also be used. In such a case, a polyurethane-based hot-melt adhesive is preferable.

The stretchable wire 11 includes a stretchable core 15 and an electrically conductive wire 16 wound around the core 15, for example. Accordingly, the stretchable wire 11 can stretch as following the core 15 stretches. The core 15 is arranged along the longitudinal direction of the wire tape 3, and the thickness of the core 15 is preferably 10 to 4000 dtex (deci-tex), more preferably, 300 to 2000 dtex, and further preferably, 500 to 1500 dtex from the perspective of durability. In addition, only one core 15 or more than one core 15 may be provided. A smaller number of cores 15 can reduce tensile strength, while bundling a plurality of thin wires can control the diameter of the electrically conductive wire more easily. Considering them altogether, the number of the cores 15 is preferably 1 to 4, or more preferably, 2 to 3. Examples of the materials of the core 15 include wires and fibers made of natural rubber or synthetic rubber. Among them, polyurethane rubber and polyester rubber are preferable from the perspectives of heat resistance, durability, and cost. The stretchability of the core 15 is such that the amount of change in the shape of the core 15 from the initial shape is preferably greater than or equal to 100%, or more preferably, greater than or equal to 200%. Winding the electrically conductive wire while pulling the core 15 can reduce tension that would act when the wire tape 3 is stretched.

As the material of the electrically conductive wire 16, an electrically conductive yarn or an electrically conductive wire can be used. "Electrically conductive yarns" as used in this specification refer to yarns with electrical conductivity, specifically, those obtained by covering natural fibers or chemical fibers with an electrically conductive material, while "electrical conductive wires" refer to linear members made of electrically conductive materials. Electrically conductive wires are typically metal wires, but are not limited to metal wires as long as they are wires with electrical conductivity.

As the electrically conductive yarns, those obtained by coating non-electrically conductive yarns, such as natural fibers or chemical fibers, with an electrically conductive material through plating or dipping, for example, can be used. Among them, electrically conductive yarns coated with silver are preferable, and as the non-electrically conductive yarns, polyester and nylon yarns are preferable. The electrically conductive yarns have high durability and high trackability in response to changes in the shape. Therefore, the electrically conductive yarns can withstand deformations of textiles and the like.

Aluminum, copper, silver, tungsten, or gold is preferably used for the electrically conductive wires. In particular, copper is more preferably used, taking into consideration workability, cost, and durability altogether, for example. As the electrically conductive wires have low electrical resistance, they are preferably used for wires of digital sensors for which high electrical conductivity is required. Further, alloys of such metals can also be used. When alloy is used, its resistivity is preferably less than or equal to 5.00 ($\times 10^{-6}$ $\Omega \cdot$cm), further preferably, less than or equal to 3.00 ($\times 10^{-6}$ $\Omega \cdot$cm), or most preferably, 2.00 ($\times 10^{-6}$ $\Omega \cdot$cm). Specific examples of alloys include beryllium copper, copper zirconium, brass, bronze, phosphor bronze, titanium copper, and cupro-nickel. Further, such metal wires can be plated. Specific examples of metals used for plating include tin, zinc, copper, silver, nickel, aluminum, titanium, platinum, gold, and alloys thereof.

For the electrically conductive wire 16, the one obtained by twisting an electrically conductive wire and an electrically conductive yarn or non-electrically conductive yarn together can also be used. This can improve durability in comparison with when an electrically conductive wire is used alone. The direction of twist herein may be either Z-twist or S-twist, and the directions of twists of the electrically conductive wire and the electrically conductive yarn or the non-electrically conductive yarn may be either the same or opposite. The electrically conductive yarn 16 may be not only a plied yarn formed by twisting single twist yarns together but also a corkscrew twist yarn formed by combining a single twist yarn and a non-twist yarn, a covering yarn having a yarn wound on its outer most layer, or a yarn formed by repeatedly twisting yarns together. In addition, the electrically conductive wire 16 may be formed by twisting three or more yarns together.

The hot-melt bonding layer 14 is provided on one of the upper and lower stretchable insulating films 12 on the side opposite to the bonding layer 13 in order to bond the wire tape 3 and the substrate 1 together. The hot-melt bonding layer 14 contains a material that melts with heat applied thereto, and is typically called a hot-melt adhesive. Preferably, a stretchable hot-melt adhesive is used. Examples of the stretchable hot-melt adhesive include polyurethane-based hot-melt adhesives. Accordingly, the wire tape can have improved stretchability.

Figure 4:
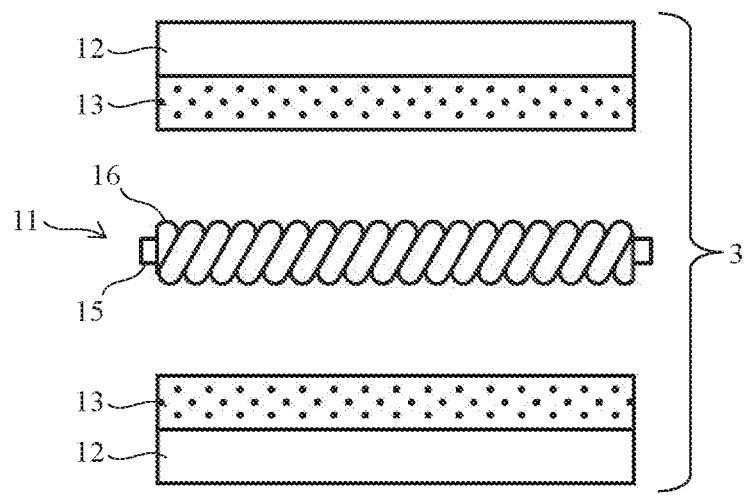
FIG. 4 illustrates a modified example of the first embodiment.

The hot-melt bonding layer 14 may be formed on one of the stretchable insulating films 12 in advance, or may be supplied to the gap between the stretchable insulating film 12 and the substrate 1 from a different production system during a bonding operation without being formed on the stretchable insulating film 12, as illustrated in FIG. 4.

Figure 5:
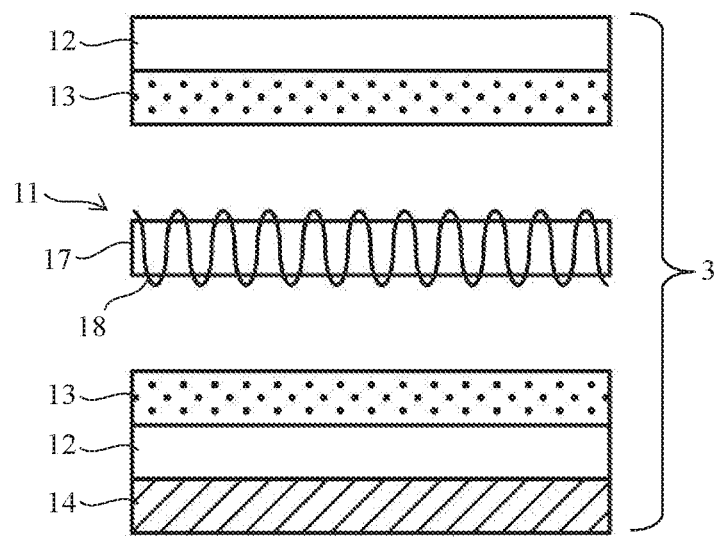
FIG. 5 illustrates a modified example of the first embodiment.

FIG. 5 illustrates the structure of the wire tape 3 according to a modified example of the first embodiment. In the wire tape 3 of FIG. 5, the stretchable wire 11 includes a stretchable insulating film 17 parallel with the plane of each stretchable insulating film 12, and an electrically conductive wire 18 formed so as to vertically penetrate through the stretchable insulating film 17 beyond the upper and lower faces thereof. Exemplary methods of forming the wire tape 3 include a method of sewing the electrically conductive wire 18 into the stretchable insulating film 12 through hand-stitching or using a sewing machine or an embroidering machine, for example. Selecting a thin needle or an electrically conductive wire 18 with a small frictional force can suppress tears of the stretchable insulating film 12. Examples of the sewing methods include blind stitching that includes passing a needle through the inside of the film from one face of the film and taking the needle out of the same face of the film where the needle has been inserted. However, since the stretchable wire 11 with the core 15 in the examples of FIGS. 3 and 4 can typically have a smaller width, the stretchability of such stretchable wire 11 is higher. Meanwhile, since the density of the electrically conductive wire 18 can typically be increased, electrical conductivity is also increased. In addition, a sewing pattern of the electrically conductive wire 18 preferably includes a serpentine shape within the plane of the film. Accordingly, even when the stretchable insulating film 17 stretches in the longitudinal direction, the electrically conductive wire 18 can also stretch correspondingly. Therefore, advantageous effects approximately the same as those obtained with the configuration of FIG. 4 can be obtained. The serpentine shape may be any shape, such as a zigzag shape, a wave shape, a curved line obtained by arranging a plurality of horseshoe shapes and/or parts of horseshoe shapes and joining the ends thereof together or interpolating them, consecutive hairpin curves, a line formed by combining parts of a plurality of polygons, a line formed by combining parts of a plurality of star shapes; a combination of them; an approximate straight line or an approximate curved line of them; a combination of the aforementioned lines and an approximate straight line or an approximate curved line of them. The period and width of the serpentine shape may have any values. Further, the serpentine shape may include various shapes, periods, and/or widths.

Figure 6:
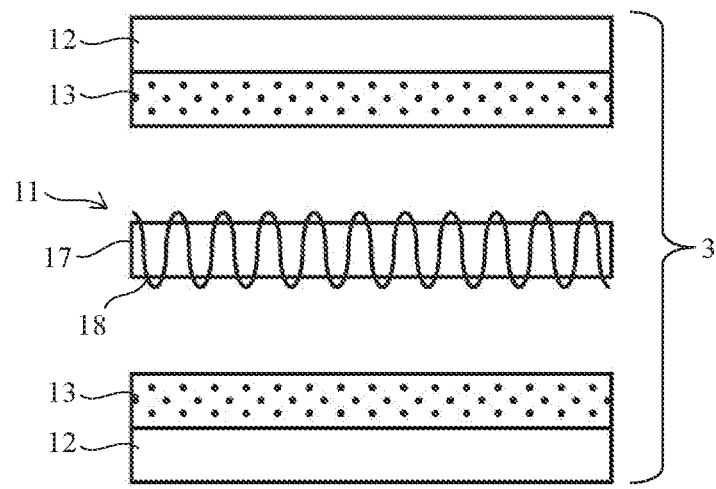
FIG. 6 illustrates a modified example of the first embodiment.

In the configuration of FIG. 5 also, the hot-melt bonding layer 14 may be supplied to the gap between the stretchable insulating film 12 and the stretchable substrate 1 from a different production system during a bonding operation without being formed on the stretchable insulating film 12, as illustrated in FIG. 6.

The thickness of the stretchable insulating film 17 is preferably 5 to 300 μm, or more preferably, 10 to 100 μm. The thickness in such a range can maintain high stretchability and strength. Examples of the materials of the stretchable insulating film 17 include wires and fibers made of natural rubber and synthetic rubber. Among them, polyurethane rubber and polyvinyl chloride rubber are preferable from the perspectives of heat resistance, durability, and cost.

Figure 7:
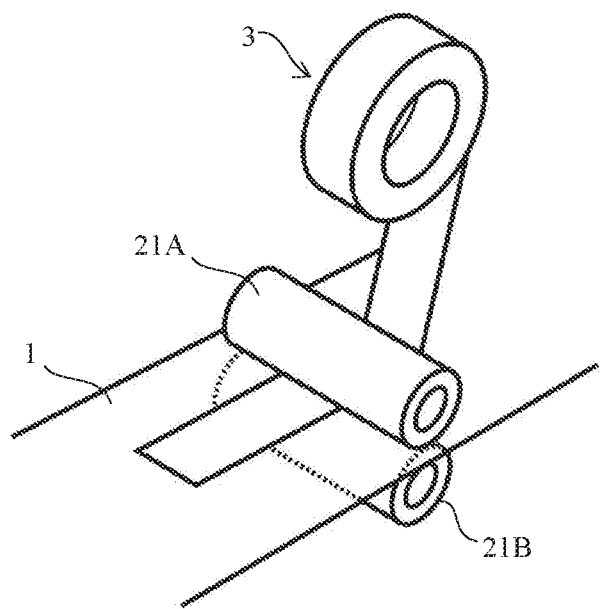
FIG. 7 illustrates a method for producing a wearable device 100 (i.e., a textile having wires) according to the first embodiment.

FIG. 7 is a schematic perspective view illustrating a method for producing a textile having wires by bonding the wire tape 3 of the first embodiment to the substrate 1. In the operation of bonding the wire tape 3, first, the substrate 1 and the wire tape 3 are inserted into the gap between a pair of a heat roller 21A and a feed roller 21B of a heat welder. At this time, if the wire tape 3 has the hot-melt bonding layer 14, the wire tape 3 is disposed such that the hot-melt bonding layer 14 is opposite the substrate 1. The heat roller 21A is configured to be rotatable by a motor (not illustrated), while the feed roller 21B is not coupled to a motor and merely functions as a transport mechanism that merely rotates passively with the drive of the heat roller 21A. In addition, the heat roller 21A includes a heater (not illustrated) and is configured to be able to heat the wire tape 3, while the feed roller 21B does not include a heater.

Opposite sides of the substrate 1 and the wire tape 3 are sandwiched between the heat roller 21A and the feed roller 21B at a predetermined pressure so as to be heated by the heat roller 21A. Accordingly, the hot-melt bonding layer 14 (or a separately supplied hot-melt adhesive) melts and is cooled to solidify again so that the substrate 1 and the wire tape 3 are coupled together. Examples of the heat source include electric heaters and frictional heat due to ultrasound.

It should be noted that the example of FIG. 7 is only exemplary, and the feed roller 21B may be replaced with a roller driven by a motor so that the motors that are driven by two respective drivers may be used. Alternatively, the feed roller 21B may be replaced with a heat roller so that the wire tape 3 can be heated from its upper and lower sides. Further, instead of the feed roller, other transport mechanisms, such as flat plates or conveyer belts, may be used. Although the heat roller 21A and the feed roller 21B may be fixed so as to move the substrate 1 and the wire tape 3, the heat roller 21A and the feed roller 21B may instead be configured to be movable with respect to the fixed substrate and wire tape 3.

Figure 8:
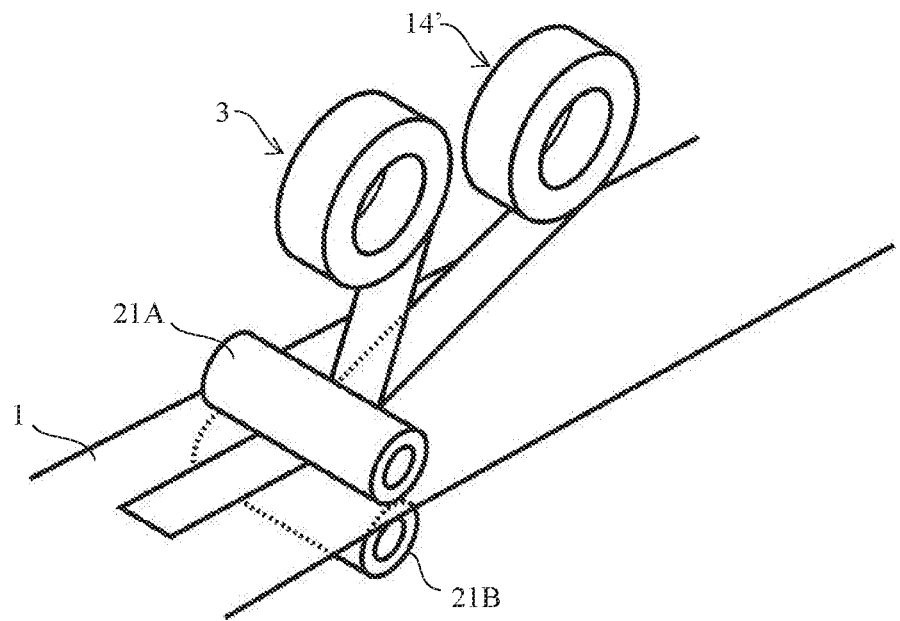
FIG. 8 illustrates a modified example of the method for producing the wearable device 100 (i.e., a textile having wires) according to the first embodiment.

It should be noted that in the case of the wire tape 3 without the hot-melt bonding layer 14 (FIG. 4), a separate hot-melt adhesive tape 14' may be inserted into the gap between the wire tape 3 and the substrate 1 as illustrated in FIG. 8, and procedures similar to those in FIG. 7 can be executed. Various modifications are possible as in FIG. 7.

Advantageous Effects

Advantageous effects of the first embodiment will be described. In the wire tape 3 of the first embodiment, the stretchable wire 11 is formed along the longitudinal direction of each stretchable insulating film 12, and the width in the shorter-side direction of the stretchable insulating film 12 can be set to about 5 to 20 mm, for example. With such a width, the stretchable wire 11 can be protected. Since the wire tape 3 has such dimensions, a wire can be formed on the substrate 1 in accordance with a predetermined wire layout.

In the wearable device, wires with various shapes are required to be formed in accordance with the portions of a human body to be detected or the types of operations to be detected. It is acceptable as long as the width in the shorter-side direction of each wire tape 3 of the present embodiment is small but is large enough to cover the stretchable wire 11. Therefore, the wire tape 3 may be provided with a curvature so as to be bonded to the substrate 1. Thus, wires with desired layouts can be easily produced and the diversity of the wearable device can be improved.

Further, according to the wire tape 3 of the first embodiment, a waste of materials can be minimized. That is, sequentially heating the wire tape 3 and thus bonding it to the substrate 1 in accordance with a desired wire layout of the wearable device can form desired wire patterns of the wearable device. In such a case, unnecessary portions need not be cut away from the wire tape 3, for example, thus, generating no waste members.

Second Embodiment

Figure 9:
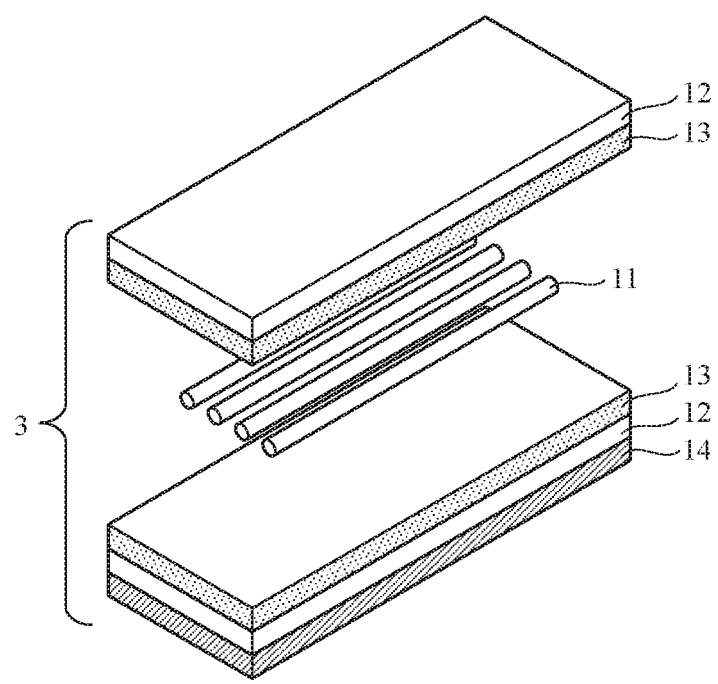
FIG. 9 is a schematic view illustrating the configuration of a wire tape 3 according to the second embodiment.

Next, the wire tape 3 according to the second embodiment of the present invention will be described with reference to FIG. 9. The wire tape 3 differs from that of the first embodiment in the arrangement of the stretchable wire 11. Bonding the wire tape 3 to the substrate 1 can produce a wearable device similar to that of the first embodiment.

In the wire tape 3 of the second embodiment, a plurality of stretchable wires 11 are arranged approximately in parallel at a predetermined pitch along the shorter-side direction of each stretchable insulating film 12 so that the stretchable wires 11 do not contact each other. The structure of each stretchable wire 11 may be the same as that of the first embodiment or the modified example of the first embodiment. The plurality of stretchable wires 11 are spaced apart from each other so as not to contact each other, and further, opposite faces of the stretchable wires 11 are sandwiched between the stretchable insulating films 12 so that electrical insulation can be secured.

Third Embodiment

Figure 10:
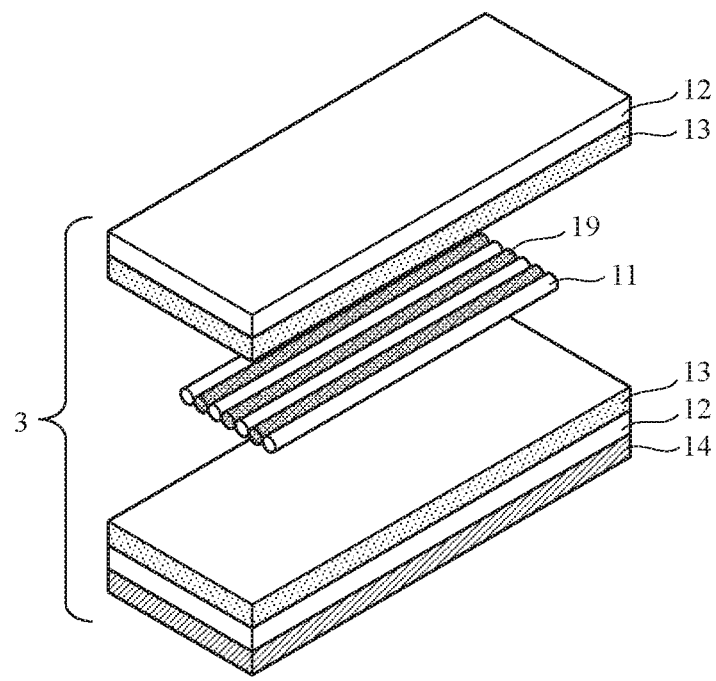
FIG. 10 is a schematic view illustrating the configuration of a wire tape 3 according to the third embodiment.

Next, the wire tape 3 according to the third embodiment of the present invention will be described with reference to FIG. 10. The wire tape 3 differs from that of the previous embodiment in the arrangement of the stretchable wires 11. Bonding the wire tape 3 to the substrate 1 can produce a wearable device similar to those of the first and second embodiments.

In the wire tape 3 of the third embodiment, a plurality of stretchable wires 11 are arranged approximately in parallel at a predetermined pitch along the shorter-side direction of the stretchable insulating film 12, and stretchable non-electrically conductive wires 19 are arranged in the gaps between the plurality of stretchable wires 11. The structure of each stretchable wire 11 may be the same as that of the first embodiment. Meanwhile, the stretchable non-electrically conductive wires 19 may have an insulating property as a whole and are arranged at positions between the plurality of stretchable wires 11 so as to secure electrical insulation between the plurality of stretchable wires 11. Examples of the stretchable non-electrically conductive wires 19 include wires and fibers made of natural rubber or synthetic rubber. Among them, polyurethane rubber and polyester rubber are preferable from the perspectives of heat resistance, durability, and cost. The stretchability of the stretchable non-electrically conductive wires 19 is such that the amount of change in the shape thereof from the initial shape is preferably greater than or equal to 30%, more preferably, greater than or equal to 50%, or further preferably, greater than or equal to 100%. In addition, as with the stretchable wire 11 (see FIG. 3), the wire tape 3 may include a stretchable insulating core and a non-electrically conductive wire wound around the insulating core. Examples of the non-electrically conductive wire include natural fibers and chemical fibers, and polyester and nylon yarns are preferable.

The wire tapes 3 of the second and third embodiments are particularly suitable for a wearable device including digital sensors. Typical analog sensors need two terminals, while typical digital sensors for communication schemes, such as I2C, SPI, and UART, need at least four terminals. Although wires corresponding to the number of the terminals are needed, if a number of wires concentrate on an area around a sensor, it will adversely affect the stretchability and air permeability of the wearable device. With the wire tape 3 of the second embodiment, a plurality of stretchable wires can be arranged within a single tape. Therefore, the wire tape 3 can be favorably connected to the aforementioned digital sensors. In addition, the pitch of terminals of a commercially available substrate, which has a digital sensor mounted thereon, is often 1.27 mm or 2.54 mm. Therefore, setting the wire pitch of the stretchable wire 11 to approximately 1.27 mm or 2.54 mm can easily allow the stretchable wire 11 to be connected a commercially available substrate.

Fourth Embodiment

Figure 11:
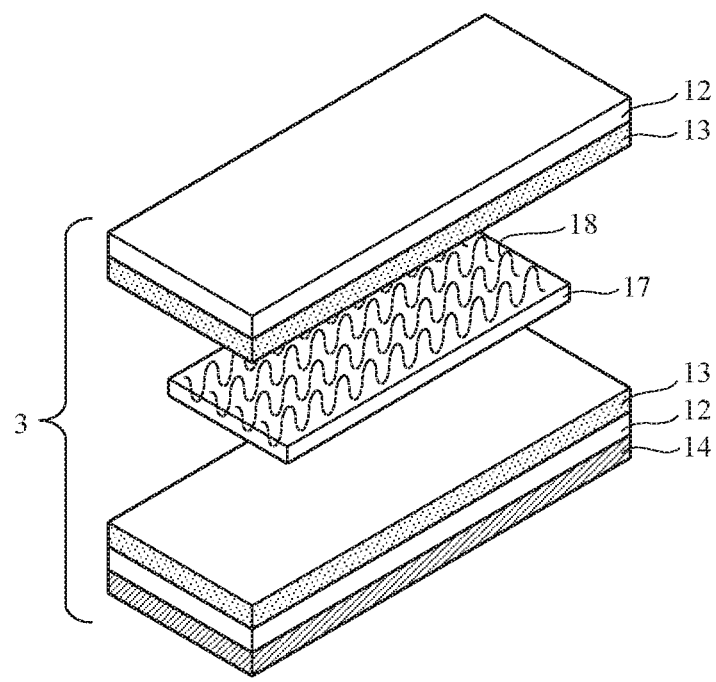
FIG. 11 is a schematic view illustrating the configuration of a wire tape 3 according to the fourth embodiment.

Next, the wire tape 3 according to the fourth embodiment of the present invention will be described with reference to FIG. 11. The wire tape 3 differs from that of the first embodiment in the arrangement of the stretchable wires 11. Bonding the wire tape 3 to the substrate 1 can produce a wearable device similar to that of the first embodiment.

In the wire tape 3 of the fourth embodiment, the stretchable wire 11 includes a stretchable insulating film 17 parallel with the plane of each stretchable insulating film 12, and electrically conductive wires 18 sewn into the stretchable insulating film 17 (so as to penetrate therethrough beyond the upper and lower faces thereof) using a sewing machine, for example, as in the modified example of the first embodiment (FIG. 5). However, the electrically conductive wires 18 are arranged approximately in parallel at a predetermined pitch along the shorter-side direction of each stretchable insulating film 12 so that the plurality of electrically conductive wires 18 do not contact each other. Such a configuration also allows a plurality of wires to be arranged within a single wire tape 3 as in the second and third embodiments.

Although several embodiments of the present invention have been described above, they are only for illustrative purposes and are not intended to limit the scope of the invention. Such novel embodiments can be implemented in various different ways, and can be omitted, replaced, or changed without departing from the spirit and scope of the invention. Such embodiments and modified examples thereof are encompassed within the spirit and scope of the invention and within the invention recited in the claims as well as equivalents thereof.

What is claimed is:

1. A stretchable wire tape for a textile, comprising:
   a stretchable electrically conductive wire;
   stretchable insulating films each including a first face and a second face opposite to the first face, the stretchable insulating films being bonded to opposite sides of the stretchable electrically conductive wire on their first faces via bonding layers; and
   at least one stretchable non-electrically conductive wire, wherein
   the stretchable electrically conductive wire includes a plurality of stretchable electrically conductive wires, and
   the stretchable electrically conductive wires and the at least one stretchable non-electrically conductive wire are alternately arranged.

2. The stretchable wire tape for the textile according to claim 1, further comprising a hot-melt bonding layer formed on the second face of each stretchable insulating film.

3. The stretchable wire tape for the textile according to claim 1, wherein the stretchable electrically conductive wire includes a stretchable core and at least one electrically conductive wire wound around the stretchable core.

4. The stretchable wire tape for the textile according to claim 1, wherein the stretchable electrically conductive wire includes a stretchable insulating substrate and an electrically conductive wire formed to penetrate through the insulating substrate beyond upper and lower faces of the insulating substrate.

5. The stretchable wire tape for the textile according to claim 1, wherein the stretchable electrically conductive wire includes a plurality of stretchable electrically conductive wires that are arranged approximately in parallel without being in contact with each other.

6. The stretchable wire tape for the textile according to claim 5, wherein the stretchable electrically conductive wires are arranged at a pitch of approximately 1.27 mm or 2.54 mm.

7. A wearable device comprising:
   a stretchable electrically conductive wire tape bonded to a substrate; and
   a plurality of sensors connected to the stretchable electrically conductive wire tape,
   wherein the stretchable wire tape includes
   a stretchable electrically conductive wire,
   stretchable insulating films each including a first face and a second face opposite to the first face, the stretchable insulating films being bonded to opposite faces of the stretchable electrically conductive wire on their first faces via bonding layers; and
   at least one stretchable non-electrically conductive wire, wherein
   the stretchable electrically conductive wire includes a plurality of stretchable electrically conductive wires, and
   the stretchable electrically conductive wires and the at least one stretchable non-electrically conductive wire are alternately arranged.

8. A method for producing a textile having wires, comprising bonding a stretchable wire tape to a substrate by melting a hot-melt bonding layer,
   wherein the stretchable wire tape includes a stretchable electrically conductive wire and stretchable insulating films, and
   the stretchable insulating films each include a first face and a second face opposite to the first face and being bonded to opposite faces of the stretchable electrically conductive wire on their first faces via bonding layers,
   further wherein the hot-melt bonding layer is melted using a heat welder, the heat welder including at least one thermal head and at least one transport mechanism.

* * * * *